United States Patent [19]

Fisher

[11] 4,063,898
[45] Dec. 20, 1977

[54] COMBUSTIBLE GASES DETECTOR

[75] Inventor: Edward William Fisher, Alliance, Ohio

[73] Assignee: Bailey Meter Company, Wickliffe, Ohio

[21] Appl. No.: 724,682

[22] Filed: Sept. 20, 1976

[51] Int. Cl.² .................. G01N 25/20; G01N 25/30; G01N 31/10; H01L 35/00
[52] U.S. Cl. .............. 23/254 E; 23/232 E; 23/255 E; 73/15 B; 73/25; 136/225
[58] Field of Search ............. 23/254 E, 255 E; 73/25, 73/15 B; 136/225; 60/276

[56] References Cited

U.S. PATENT DOCUMENTS

| 3,076,697 | 2/1963 | Miller et al. | 23/254 E |
| 3,801,973 | 4/1974 | Grabiel et al. | 60/276 X |
| 3,844,920 | 10/1974 | Burgett et al. | 60/276 X |
| 3,847,778 | 11/1974 | Riddel | 60/276 X |
| 3,906,721 | 9/1975 | Micheli et al. | 23/254 E X |
| 4,029,472 | 6/1977 | Micheli et al. | 60/276 X |

*Primary Examiner*—Morris O. Wolk
*Assistant Examiner*—Michael S. Marcus
*Attorney, Agent, or Firm*—Vytas R. Matas; Joseph M. Maguire

[57] ABSTRACT

A differential thermocouple combustible gas detector is provided by coating one thermocouple junction of a differential thermocouple pair with a catalyst and the other thermocouple junction with a non-catalyst. Heated combustible gases react with the catalyst to liberate heat to the catalyst coated thermocouple junction in proportion to the concentration of combustible gases and proportionally raise the temperature of that junction above the non-catalyst coated junction. The output signal from the differential thermocouple device is thus a signal indicative of the concentration of combustible gases.

12 Claims, 4 Drawing Figures

COMBUSTIBLE GASES DETECTOR

BACKGROUND OF THE INVENTION

1. Field of the Invention

The present invention relates to combustibles detectors generally and particularly to differential thermocouple devices modified to detect combustible gases.

2. Description of the Prior Art

Combustible gases detectors are known which utilize electrically heated platinum filaments exhibiting resistance changes in response to variable concentrations of combustible gases. The resistance change of such devices is notoriously small requiring their use in a Wheatstone bridge arrangement. This arrangement increases the cost of the device. An example of such a device may be found in U.S. Pat. No. 3,092,799 issued June 4, 1963 to A. R. Baker.

Along with the required use of a Wheatstone bridge these known devices have other shortcomings. A constant current power supply or other regulated excitation source is required and the devices exhibit drift rates which are too large to permit industrially stable operation at low combustibles concentrations. Part of the drift problem comes about because the nominal resistance value of these sensors is the order of 1.00 ohm and the presence of combustibles causes typical resistance increases to 1.04 ohms. Resistance changes of this magnitude are too close in size to the kinds of changes experienced due to fluctuations in contact resistance, electromigration, grain growth, etc.

Differential thermocouples are also known for use in thermal analysis as evidenced by U.S. Pat. No. 3,491,581 issued Jan. 27, 1970 to F. E. Roberts. However the applicant is unaware of any prior art device using such differential thermocouples coated with a catalyst and a non-catalyst to provide a self-powered, inexpensive and stable combustible gases detector.

SUMMARY OF THE INVENTION

In accordance with the present invention a differential thermocouple combustible gases detector is provided which is inexpensive, compact, self-powered and stable. One thermocouple junction of a thermocouple pair is coated with catalytic material such as platinum to allow heated combustible gases such as carbon monoxide to chemically react with the catalyst to liberate heat and to raise the temperature of the coated thermocouple junction above ambient in proportion to the concentration of the combustible gases. The other thermocouple junction of the thermocouple pair is coated with a non-catalytic material such as a refractory cement to prevent any reaction at that junction allowing that junction to only monitor ambient temperature. The connection of the thermocouple pair in opposition allows the ambient temperature signals sensed by both thermocouple junctions to cancel leaving only the temperature increase over ambient caused by the reaction of combustible gases with the catalyst on the catalyst coated thermocouple junction. The differential thermocouple thus establishes a signal proportional to the concentration of combustible gases independent of the ambient temperature.

In one specific embodiment of the invention the catalyst coated junction is formed by crimping a platinum tube around the junction and then coating the tube with platinum paste to further increase the surface area of the catalyst. The non-catalyst junction is formed by crimping a soft metal tube such as a brass tube around the junction and coating the tube with refractory cement.

In certain situations the combustible gases may have to be heated to a threshold temperature at which they will react with the catalyst. A coil heater is then mounted around the two thermocouple junctions to heat the combustible gases. Since sulfur is present in some mixtures containing combustible gases the catalyst must be maintained above the dew point of sulfuric acid to prevent condensation of the acid on the catalyst and the "poisoning" of the catalyst. In such situations the heater output is raised to maintain the ambient temperature of the junctions at approximately 800° F.

In view of the foregoing it will be seen that one aspect of the present invention is to provide a differential thermocouple combustible gases detector.

Another aspect of the present invention is to provide a heated combustible gases detector which will insure that the combustible gases are above the reaction threshold temperature and prevent acid condensation on the catalyst.

These and other aspects of the present invention will be more fully understood upon consideration of the following description of the preferred embodiment in conjunction with the associated drawings.

DESCRIPTION OF THE PREFERRED EMBODIMENT

Figure 2:
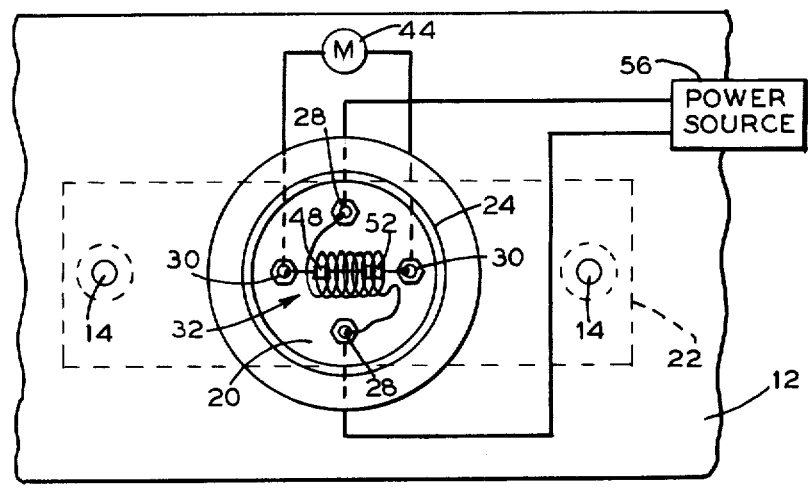
FIG. 2 is a bottom plan view of the FIG. 1 detector.
Figure 1:
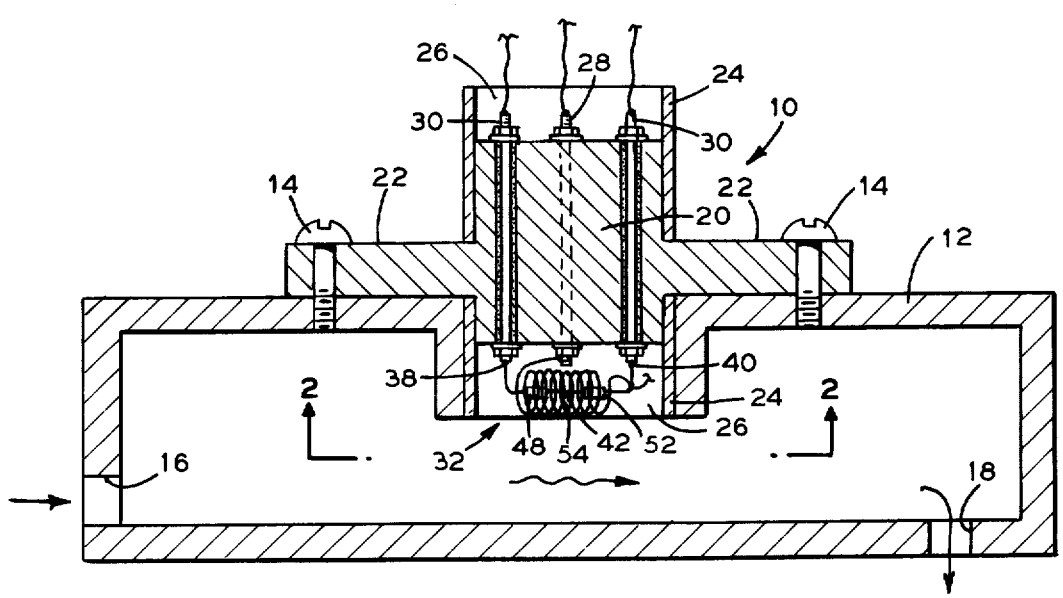
FIG. 1 is a side view of the combustible gases detector of the present invention.

Referring now to the drawings, FIGS. 1 and 2 disclose a combustible gases detector assembly 10 mounted to a block 12 by screws 14. The block 12 is designed to allow flue gases which include air diluted combustible gases to flow through the block 12 from an inlet 16 to an outlet 18 so as to come in contact with the detector assembly 10. The block 12 may be a part of a complete gas sampling analyzing system also including an oxygen detector as is described in U.S. Pat. No. 3,960,500 issued June 1, 1976 which provides for recirculation of flue gases from a duct and back thereto. Further details of such a gas sampling analyzing system are available in the mentioned patent and the reader is referred thereto for any further required clarification.

The detector assembly 10 includes a metal block 20 having mounting flanges 22 through which the screws 14 sealably mount the detector assembly 10 to the block 12. Thin wall tubing 24 is pressed onto the block 20 on both ends of the flanges 22 to extend beyond the ends of the metal block 20 and to provide a protected space 26 at both ends of the metal block 20. Two pairs of electrical leads 28 and 30 are extended through the block 20 to be electrically isolated therefrom and to have ends extending into the spaces 26. The electrical leads 28 and 30 are brass with gold flash; however, nickel has also been found to be a suitable material.

The heart of the detector assembly 10 is a differential thermocouple assembly 32 connected across the electrical leads 30.

Figure 3:
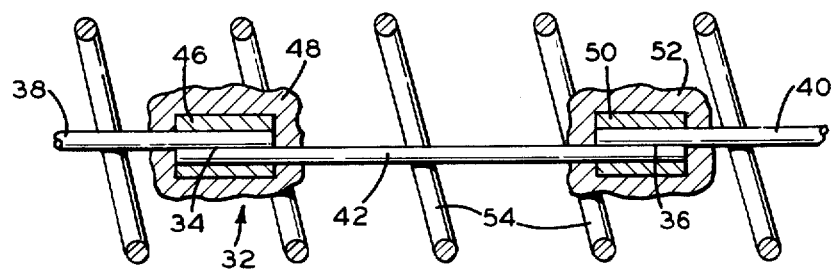
FIG. 3 is an expanded cut-away side view of the thermocouple junctions of the FIG. 1 detector.

As may be best seen in FIG. 3, the differential thermocouple assembly 32, a first thermocouple junction 34, and a second thermocouple junction 36 is provided by overlapping the ends of alumel wires 38 and 40 with a common connecting wire 42 of chromel. As is known, the thermocouple junctions 34 and 36 will induce opposing millivoltage signals depending on the temperatures of the respective junctions 34 and 36. These millivoltage signals will be transmitted along the electrical leads 30 by virtue of the connection of the thermocouple assembly 32 thereto to a voltmeter 44 connected to the opposite ends of the electrical leads 30. To have the thermocouple assembly 32 act as a combustible gases detector, the respective thermocouple junctions 34 and 36 must be coated with catalytic material and non-catalytic material. To accomplish this, as well as allow for ease of manufacture, the thermocouple junction 34 is formed by threading the ends of the chromel wire 38 and one end of the alumel wire 42 into a platinum tube 46 and crimping the platinum tube 46 onto the ends of the mentioned wires. Platinum is a known catalytic material and is used in the preferred embodiment, although other known material such as palladium could also have been used. To further increase the surface area of the catalyst, platinum paste 48 is coated around the platinum tube 46 and the assembly baked at 1000° F to solidify the paste and to form a catalytic thermocouple junction.

The thermocouple junction 36 is formed into a non-catalytic thermocouple junction by threading the ends of the chromel wire 40 and the common alumel wire 42 into a brass tube 50 and crimping the tube 50 onto the thermocouple junction 36 to retain it thereto. To further insure the non-catalytic aspects of the thermocouple junction 36, the brass tube 50 is coated with a resistor cement 52 which is known as Sauereisen No. 7 resistor cement commercially available and being composed of aluminum oxide and silicon oxide among other elements. Coating the brass tube 50 with resistor cement matches the thermal mass of the non-catalytic junction with that of the catalytic junction to equalize the transient thermal response of the two junctions.

The ability of the described catalytic and non-catalytic coated thermocouple junctions to operate as a combustible gases detector rests on the fact that combustibles such as carbon monoxide and methane will react with oxygen in the presence of a heated catalyst such as platinum to form carbon dioxide and liberate heat to the catalyst according to the following chemical equations;

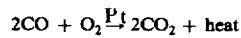

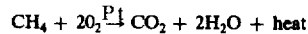

The catalyst must be heated to a threshold temperature at which the above reactions take place. For platinum this threshold temperature is around 400° F.

To insure that the gases flowing through the catalytic and non-catalytic coated thermocouple junctions are above the threshold temperature of 400° F a spiral heater 54 is wrapped around the catalytic coated thermocouple junction 34 and the non-catalytic coated thermocouple junction 36. The heater 54 is connected across the electrical leads 28 with the opposite ends of the electrical leads 28 being connected to a suitable power source 56 which provides energy to the heater 54. Since sulfur dioxide is present along with certain combustible gases in the combustion of fossil fuels, a problem of poisoning the catalyst 48 may occur. Sulfur dioxide may react with hydrogen to form sulfuric acid which could condense on the platinum paste and cause the catalytic action to deteriorate. The applicant has found that by setting the heater 54 to maintain a temperature of approximately 800° F in the ambient of the catalytic coated thermocouple 34, the thermocouple 34 is maintained at a temperature at which the sensor 10 output is substantially linear. This temperature is also above the normal dew point of sulfuric acid, thereby preventing condensation of the acid onto the catalytic surface and preventing deterioration of the catalyst thereby.

Figure 4:
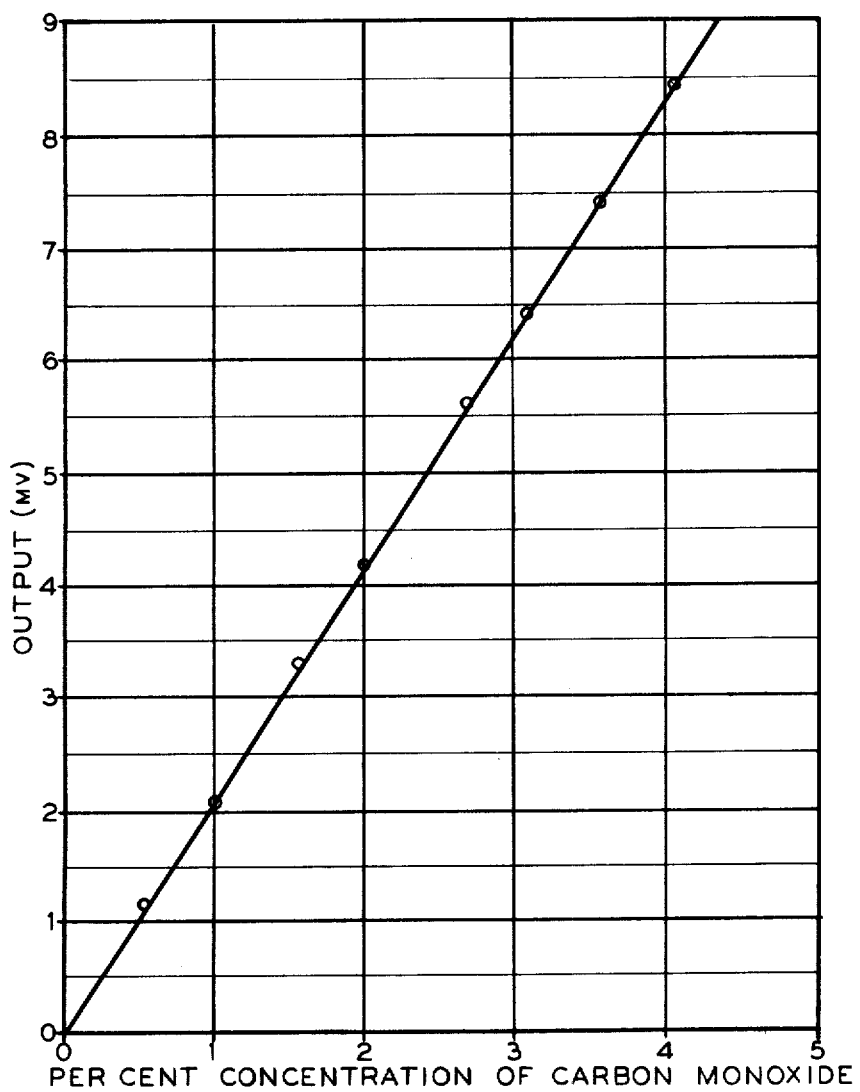
FIG. 4 is a graphical representation of the output signal variation of the FIG. 1 detector in response to CO concentration in a gas mixture.

From the foregoing it will be now readily seen that the thermocouple assembly 32 is ideally suited to monitor combustibles in the flue gases entering the inlet 16 and exiting through the outlet 18. Depending on how complete the combustion in the combustion process will be, different amounts of combustible gases such as carbon monoxide will be produced. The carbon monoxide will react with the platinum on the catalytic coated thermocouple junction 34 to produce carbon dioxide and liberate heat to the catalytic coated thermocouple junction 34. The more carbon monoxide is present in the flue gases, the more carbon dioxide will be produced and the more heat will be liberated to the catalytic coated thermocouple junction 34. The non-catalytic coated thermocouple junction 36 will not provide any kind of a reaction liberating heat to the junction 36 and as such will only measure the ambient temperature common to both the non-catalytic coated thermocouple junction 36 and the catalytic coated thermocouple junction 34. Because of the electrical connection of the two coated thermocouple junctions 34 and 36 and their sharing of a common ambient temperature, the ambient temperture effect will be cancelled out, leaving only the temperature rise above ambient produced at the catalytic coated thermocouple junction 34 as a result of the chemical reaction occurring at the platinum surface 48. Referring to FIG. 4, it may be seen that varying concentrations of carbon monoxide will produce a corresponding variable millivoltage output at the voltmeter 44 as a result of the variable heat liberated to the catalytic coated thermocouple junction 34 dependent on the concentration of carbon monoxide in the flue gases. The millivoltmeter 44 may be thus calibrated according to the chart disclosed in FIG. 4 to provide a direct readout of the percent concentration of combustible gases such as carbon monoxide in the flue gases passing by the detector assembly 10.

To insure that no other catalytic reaction occurs at various elements of the detector assembly 10 which would influence the measure of combustible gases by the detector assembly 10, special care must be taken in the choice of metals used for forming the thermocouple junctions or the heater. As a precaution, the Applicant has found it desirable to coat the heater 54 with resistor cement such as Sauereisen. Similarly, there is a possibility that the chromel-alumel thermocouple wires may be attacked by sulfuric acid fumes. As a precaution from such attack as well as to prevent any possible catalytic reaction on the wires, such wires could also be coated with Sauereisen resistor cement. It may also be desirable to use other materials for the thermocouple wires such as Platinel I and II, which are a well-known platinum material thermocouple wire. The use of such Platinel wires would very difinitely require the coating of such wires with resistor cement such as Sauereisen because of the catalytic action that would occur on such wires.

Certain modifications and improvements will occur to those skilled in the art upon reading this Specification. It will be understood that all such improvements and modifications have been deleted herein for the sake of conciseness and readability but are properly within the scope of the following claims.

What I claim is:

1. A detector for monitoring combustible gases in an airstream comprising:
   a first thermocouple junction located in the airstream;
   a second thermocouple junction located in the airstream and connected to said first thermocouple to form a differential thermocouple;
   catalytic means formed around said first thermocouple junction allowing heated combustibles in the airstream to react with said catalytic means to liberate heat and increase the temperature of said first thermocouple above that of said second thermocouple;
   insulation means formed around said second thermocouple junction to prevent combustibles in the airstream from reacting with said second thermocouple junction to liberate heat including a tube of non-catalytic material mounted on said second thermocouple junction with a non-catalytic cement material formed around said non-catalytic tube; and
   means connected to said first and second thermocouple junctions for indicating the temperature differential between said first and second thermocouple junctions.

2. A detector as set forth in claim 1 wherein said catalytic means includes a platinum tube mounted on said first thermocouple junction.

3. A detector as set forth in claim 1 wherein said catalytic means includes a platinum paste baked onto said first thermocouple junction.

4. A detector as set forth in claim 1 wherein said catalytic means includes a platinum tube mounted on said first thermocouple junction and a coating of platinum paste baked onto said platinum tube to increase the catalytic surface area thereby.

5. A detector as set forth in claim 1 including heater means for maintaining the temperature of said first and said second thermocouple junctions above a predetermined temperature below which combustibles in the airstream will not react with the catalytic means on said first thermocouple junction.

6. A detector as set forth in claim 5 wherein said heater means includes a coil heater mounted around said first and second thermocouple junction.

7. A detector as set forth in claim 6 wherein said coil heater is coated with a non-catalytic cement material to prevent combustibles in the airstream from reacting with the heater material.

8. A differential thermocouple device for detecting carbon monoxide in air comprising:
   a first thermocouple junction formed from dissimilar metals;
   a second thermocouple junction formed form the same dissimilar metals as said first thermocouple and being electrically connected to said first thermocouple to oppose the electrical output signal of said first thermocouple;
   a catalytic material tube mounted on said first thermocouple junction to react with the carbon monoxide in the air to liberate heat in proportion to the concentration of carbon monoxide and increase the temperature of said first thermocouple junction located in said catalytic material tube;
   a non-catalytic material tube located on said second thermocouple junction to prevent any reaction with the carbon monoxide in the air at the second thermocouple junction; and
   detection means connected to said first and said second thermocouple junctions to provide an output responsive to the temperature difference between said first and second thermocouple junctions to indicate the concentration of carbon monoxide thereby.

9. A device as set forth in claim 8 including a coating of platinum paste baked onto said catalytic material tube to increase the catalytic surface area thereby.

10. A device as set forth in claim 9 including a non-catalytic cement material formed around said non-catalytic material tube.

11. A device as set forth in claim 10 including heater means for maintaining the temperature of said first and said second thermocouple junctions above a predetermined temperature below which combustibles in the airstream will not react with the catalytic means on said first thermocouple junction.

12. A device as set forth in claim 11 wherein said heater means includes a coil heater mounted around said first and second thermocouple junction.

* * * * *